(12) United States Patent
Young et al.

(10) Patent No.: US 9,414,917 B2
(45) Date of Patent: Aug. 16, 2016

(54) SYSTEMS AND METHODS FOR LOADING A VALVE PROSTHESIS ONTO A CATHETER

(71) Applicant: Medtronic, Inc., Minnesota, MN (US)

(72) Inventors: Misha Young, Cupertino, CA (US); Scott Janis, Santa Rosa, CA (US); Alfonso D'Alessandro, San Francisco, CA (US); Glenn Stante, San Francisco, CA (US); Karan Punga, Santa Rosa, CA (US); Devin Gosal, Santa Rosa, CA (US); Geoffrey Orth, Sebastopol, CA (US); Cynthia Clague, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 213 days.

(21) Appl. No.: 14/029,202

(22) Filed: Sep. 17, 2013

(65) Prior Publication Data

US 2015/0081011 A1    Mar. 19, 2015

(51) Int. Cl.
*A61F 2/24* (2006.01)
*A61F 2/95* (2013.01)

(52) U.S. Cl.
CPC .............. *A61F 2/2436* (2013.01); *A61F 2/2418* (2013.01); *A61F 2002/9522* (2013.01); *A61F 2230/0067* (2013.01); *A61F 2250/006* (2013.01); *A61F 2250/0091* (2013.01); *A61F 2250/0097* (2013.01)

(58) Field of Classification Search
CPC ........... A61F 2/2436; A61F 2250/0091; A61F 2230/0067; A61F 2250/0097; A61F 2002/9522; A61F 2250/006; A61F 2/2418; A61F 2/2427; B25B 5/142; B25B 5/166; B25B 5/103
See application file for complete search history.

(56) References Cited

U.S. PATENT DOCUMENTS

| | | | | |
|---|---|---|---|---|
| 8,931,159 | B2 * | 1/2015 | Hillukka ............... | A61F 2/2427 29/508 |
| 9,021,674 | B2 * | 5/2015 | Hillukka ............... | A61F 2/0095 254/134.3 FT |
| 9,060,860 | B2 * | 6/2015 | Morris .................. | A61F 2/2436 |
| 2004/0193243 | A1 * | 9/2004 | Mangiardi ............. | A61F 2/95 623/1.11 |
| 2007/0239271 | A1 * | 10/2007 | Nguyen ................ | A61F 2/2436 623/2.11 |
| 2012/0165916 | A1 * | 6/2012 | Jordan .................. | A61F 2/95 623/1.11 |

OTHER PUBLICATIONS

U.S. Appl. No. 13/658,082, filed Oct. 23, 2012, Stante.

\* cited by examiner

*Primary Examiner* — David Bryant
*Assistant Examiner* — Lawrence Averick

(57) ABSTRACT

A medical device loading system can comprise a first housing, a second housing, and a plate. The first housing comprises a first open end, a first tapered inner surface, and a second open end. The second housing comprises a third open end, a second tapered inner surface, and a fourth open end. The second housing can define a slot between the second tapered surface and the third open end. The plate can be configured to be slidably received within the slot. The loading system can further comprise a first elongated member and a second elongated member.

20 Claims, 12 Drawing Sheets

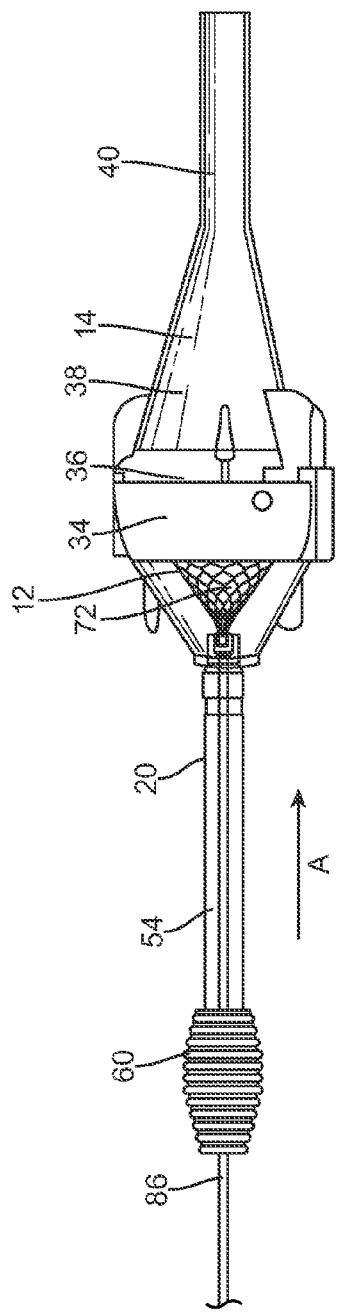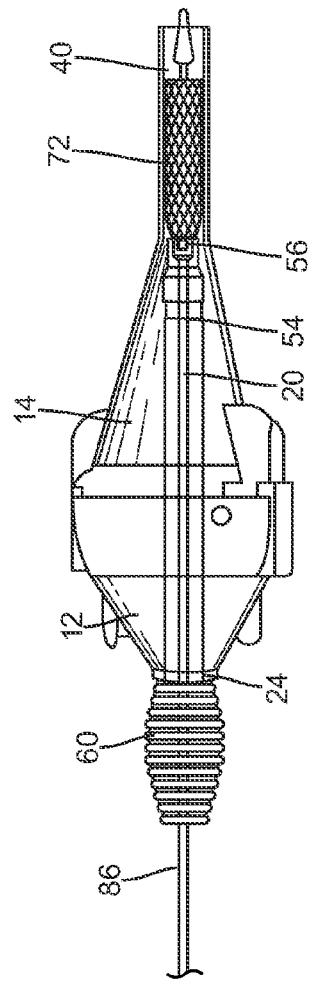
FIG. 11A
FIG. 11B

SYSTEMS AND METHODS FOR LOADING A VALVE PROSTHESIS ONTO A CATHETER

BACKGROUND

1. Field

Embodiments of the invention relate to systems and methods for loading a medical device onto a delivery device and, particularly, to systems and methods for loading a valve prosthesis onto a delivery catheter.

2. Background

Patients suffering from valve regurgitation or stenotic calcification of the leaflets can be treated with a heart valve replacement procedure. A traditional surgical valve replacement procedure requires a sternotomy and a cardiopulmonary bypass, which creates significant patient trauma and discomfort. Traditional surgical valve procedures can also require extensive recuperation times and may result in life-threatening complications.

One alternative to a traditional surgical valve replacement procedure is delivering the replacement heart valve prosthesis using minimally-invasive techniques. For example, a heart valve prosthesis can be percutaneously and transluminally delivered to an implantation location. In such methods, a heart valve prosthesis can be compressed or crimped on a delivery catheter for insertion within a patient's vasculature; advanced to the implantation location; and re-expanded to be deployed at the implantation location. For example, a catheter loaded with a compressed heart valve prosthesis can be introduced through an opening in a blood vessel, for example, the femoral artery, aortic artery, or the subclavian artery, and advanced to the heart. At the heart, the prosthesis can be re-expanded to be deployed at the aortic valve annulus, for example.

BRIEF SUMMARY

In some embodiments, a system for loading a medical device onto a delivery system can comprise a first housing, a second housing, and a plate. The first housing comprises a first open end, a tapered inner surface, and a second open end. The first open end has an inner dimension that is smaller than an inner dimension of the second open end. The second housing comprises a third open end, a second tapered inner surface, and a fourth open end. The second housing can define a slot between the second tapered surface and the third open end. The fourth open end can have an inner dimension that is smaller than an inner dimension of the third open end. The plate is slidably received within the slot. In some embodiments, the system further comprises a first elongated member and a second elongated member. In some embodiments, one or more features of the loading system are transparent to verify that a medical device is properly loaded onto a delivery device. In some embodiments, to verify that a medical device is properly loaded onto a delivery device, one or more features of the loading system have a portion that provides a magnified image of a valve prosthesis, or a portion that indicate higher stresses, for example, portions including pressure sensing films or polarized portions that show stress concentrations (e.g., by birefringence or double refraction).

In some embodiments, a method of loading a medical device onto a delivery system comprises inserting a first end of a medical device into a channel defined by a first housing such that the first end of the medical device is adjacent to a plate slidably received in a slot defined by the first housing. The method can further comprise advancing the medical device along a first tapered inner surface of a second housing. Advancing the medical device along the first tapered inner surface compresses a second end of the medical device. The method further comprises removing the plate from the slot, and advancing the medical device along a second tapered inner surface of the first housing. Advancing the medical end along the second tapered inner surface compresses the first end of the medical device.

Further features and advantages of the embodiments, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate the embodiments and, together with the description, further serve to explain the principles of the embodiments and to enable a person skilled in the relevant art(s) to make and use the embodiments.

FIGS. 3-14 illustrate a method of loading a medical device onto a delivery device according to an embodiment. Particularly, FIG. 3 is a perspective view of an inflow housing and a valve prosthesis at a loading step according to an embodiment.

FIG. 4 is a perspective view of an outflow housing, an inflow housing, and a valve prosthesis at a loading step according to an embodiment.

FIG. 5 is a perspective view of an outflow housing, an inflow housing coupled to the outflow housing, and a valve prosthesis at a loading step according to an embodiment.

FIG. 6 is an enlarged perspective view of an outflow housing, a valve prosthesis, and a first elongated member at a loading step according to an embodiment.

FIG. 7 illustrates a perspective view of a delivery device and a second elongated member at a loading step according to an embodiment.

FIG. 8 is an enlarged perspective view of a delivery device and a tip of the second elongated member at a loading step according to an embodiment.

FIG. 9 is an enlarged perspective view of an outflow housing, a valve prosthesis, a first elongated member, and a second elongated member at a loading step according to an embodiment.

FIGS. 11A-11B are perspective views of an outflow housing, an inflow housing coupled to the outflow housing, a valve prosthesis, a second elongated member, and a delivery device at loading steps according to an embodiment.

FIG. 13 is a perspective view of an outflow housing, an inflow housing coupled to the outflow housing, a second elongated member, a valve prosthesis loaded within a capsule of a delivery device at a loading step according to an embodiment.

FIG. 14 is a perspective view of a valve prosthesis loaded within a capsule of a delivery device at a loading step according to an embodiment.

Figure 1A:
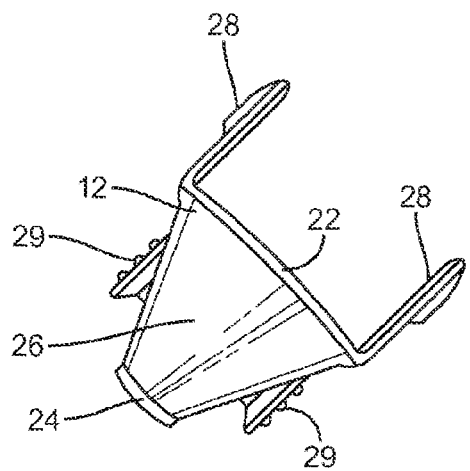
FIGS. 1A-1E illustrate a system for loading a medical device onto a delivery system, according to one embodiment, comprising an outflow housing, an inflow housing, a plate, a first elongated member, and a second elongated member.

The features and advantages of the embodiments will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The embodiments described, and references in the specification to "one embodiment," "an embodiment," "an example embodiment," "some embodiments," etc., indicate that the embodiments described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that such feature, structure, or characteristic can be used in connection with other embodiments whether or not explicitly described.

In this application, the term "inflow" is relative to the upstream or inflow side of a valve prosthesis, and the term "outflow" is relative to the downstream or outflow side of the valve prosthesis. The term "proximal" is relative to a proximal portion of the delivery device manipulated by a user and typically located outside the patient, and the term "distal" is relative to a distal end of the delivery device typically inserted within a patient. Certain features of the below described embodiments are referred to using this relative terminology. But this relative terminology is employed as a matter of convenience for the reader and is not intended as a limitation of the embodiments unless specifically recited in the appended claims.

FIGS. 1A-1E illustrate a loading system, according to an embodiment, configured to load of a valve prosthesis (not shown) onto a delivery device (not shown), for example, a minimally invasive delivery catheter. In some embodiments, the loading system is used in the operating room or cath-lab just before the delivery procedure.

In some embodiments, the loading system comprises a first outflow housing 12, a second inflow housing 14, a plate 16, a first elongated member 18 for positioning in orienting an end of a valve prosthesis, and a second elongated member 20 for housing and guiding a distal portion, for example, a capsule, of a delivery device.

Outflow housing 12 is configured to crimp one end of a medical device, for example, the outflow portion of a valve prosthesis. Crimping the one end the medical device facilitates attachment of coupling members of the medical device to the attachment member of a delivery device, for example, the delivery catheter described below with reference to FIGS. 7-14. Crimping the one end the medical device also facilitates funneling the crimped end of the medical device into a capsule of the delivery device as described below.

Outflow housing 12 defines a channel extending from a first distal open end 22 to a second proximal open end 24. Outflow housing 12 comprises a portion 26 having a tapered inner surface that has an inner dimension that decreases, and in some embodiments continuously decreases, from distal open end 22 to proximal open end 24; the inner dimension of proximal open end 24 is smaller than the inner dimension of distal open end 22. The inner dimension of proximal open end 24 is sized to allow the second elongated member 20 to pass therethrough. The inner dimension of distal open end 22 is sized to receive an end of the medical device, for example, the outflow crowns of a valve prosthesis, and crimp the end the medical device as the outflow housing 12 is moved towards the inflow housing 14. The inner dimension of distal open end 22 is sufficient to encompass the end of the medical device without damaging the medical device. The angle of the tapered surface relative to the longitudinal axis of the outflow housing 12, the inner diameter of proximal open 24, and the length between portion 26 and proximal open end 24 may vary dependent on the size or design of the medical device to ensure a consistent interface with the delivery system.

In some embodiments, portion 26 has a frustoconical inner surface. In some embodiments, portion 26 has a curved or stepped inner surface that tapers. Furthermore, although portion 26 of outflow housing 12 is generally circular in cross-section, other suitable shapes that load the medical device without damage may be employed. Additionally, although the outer surface of portion 26 has a shape that generally corresponds to the inner surface of portion 26 in FIG. 1A, in some embodiments, the outer surface does not corresponded to the tapered inner surface of portion 26.

In some embodiments, outflow housing 12 can be configured to couple with inflow housing 14. For example, in some embodiments, outflow housing 12 comprises at least one engagement tab 28 configured to selectively couple to inflow housing 14, for example, by coupling to respective cavities defined by inflow housing 14 as further explained below. As shown in FIG. 1A, outflow housing 12 can include a pair of opposing tabs 28 extending in a distal direction from distal open end 22. In some embodiments, outflow housing 12 can comprise one tab 28 or more than two tabs 28.

Outflow housing 12 can be ergonomically designed to facilitate easy handling by a user. For example, as shown in FIG. 1A, outflow housing 12 can include a plurality of gripping tabs 29. Gripping tabs 29 protrude from the exterior surface of portion 26. Users can easily place their thumbs and index fingers on tabs 29 to handle outflow housing 12.

Figure 1B:
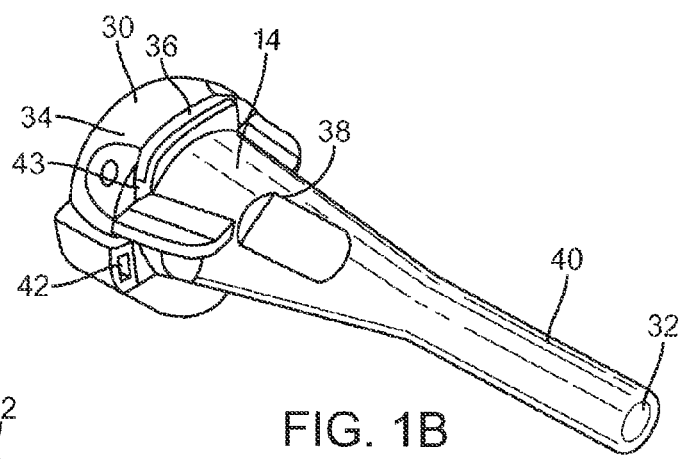

Referring to FIG. 1B, inflow housing 14 is configured to hold a medical device such that one end of a medical device can be crimped by outflow housing 12; to crimp the other end of the medical device, for example, the inflow portion of a valve prosthesis, and to hold the medical device at a crimped state until the medical device is loaded onto the delivery device. In some embodiments, inflow housing 14 defines a channel extending from a third proximal open end 30 to a fourth distal open end 32 that is configured to receive and guide an end of the medical device without damage. When inflow housing 14 is coupled to outflow housing 12, the channel extending from third proximal open end 30 to fourth distal open end 32 is coaxial with the channel extending from first distal open end 22 to second proximal open end 24. In some embodiments, the inner dimension of third proximal open end 30 is larger than the inner dimension of fourth distal open end 32.

Inflow housing 14 can comprise, in some embodiments, a first proximal portion 34 at third proximal open end 30 configured to secure, guide, and position an end of a valve prosthesis, for example, by an interference fit as described below referring to FIG. 2. For example, third proximal open end 30 can have a tapered or modified geometry that accommodates the medical device.

Inflow housing 14 defines a slot 36 in communication with the channel extending between proximal open end 30 and distal open end 32. Slot 36 is configured to slidably receive plate 16. The size and shape of slot 36 substantially corresponds to the cross-sectional shape of plate 16. For example, as shown in FIG. 1B, slot 36 is rectangular, which corresponds to the rectangular cross-sectional shape of plate 16. Slot 36 can be distal to first portion 34 and proximal open end 30 as shown in FIG. 1B.

In some embodiments, inflow housing 14 comprises a second portion 38 configured to crimp the other end of a medical device, for example, the inflow portion of a valve prosthesis, as the medical device slides against an inner surface of second portion 38. Second portion 38 has a tapered inner surface that decreases in internal diameter in the direction from third proximal open end 30 to fourth distal open end 32. In some embodiments, second portion 38 has a frustoconical inner surface. In some embodiments, portion 26 has a curved or stepped inner surface that tapers. Furthermore, although portion 26 of outflow housing 12 is generally circular in cross-sectional shape as shown in FIG. 1B, other suitable shapes may be employed. And although the outer surface of portion 38 has a shape that generally corresponds to the inner surface of portion 38 in FIG. 1B, in some embodiments, the outer surface does not corresponded to the tapered inner surface of portion 38 and can have any suitable shape. In some embodiments, slot 36 is axially between first portion 34 and second portion 38.

Inflow housing 14 can further comprise, in some embodiments, a third portion 40 configured to hold the medical device at a crimped state until the medical device is loaded on the delivery device, for example, within a capsule of a delivery catheter. Third portion 40 has a substantially cylindrical inner surface in some embodiments. In some embodiments, third portion 40 can have a tapered inner surface. Third portion 40 is adjacent and distal to second portion 38. In some embodiments, an inner dimension of third portion 40 is smaller than an inner dimension of the proximal end of second portion 38. In some embodiments, an inner dimension of third portion 40 is sized such that first elongated member 18 can pass through a medical device crimped and loaded within third portion 40 and that the medical device is crimped as much as possible before being withdrawn into a capsule of a delivery catheter. In some embodiments, the axial length of third portion 40 is substantially equal to or greater than the axial length of the medical device.

In some embodiments, first portion 34 is separate from second portion 38 and third portion 40 and coupled to second portion 38, for example, by ultrasonic welding or a snap fit. In some embodiments, first portion 34 is integral with second portion 38 and third portion 40.

Figure 1C:
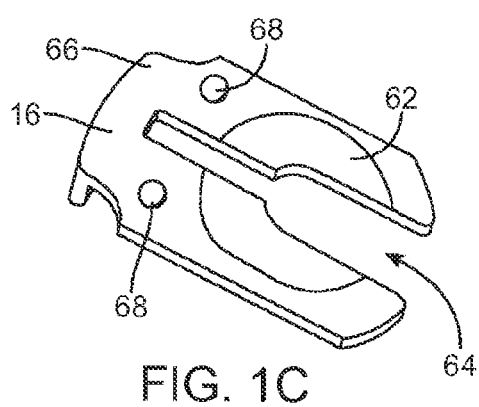

Referring to FIG. 1C, plate 16 is configured to selectively separate first portion 34 of inflow housing 14 from second portion 38 of inflow housing 14. Plate 16 is configured to be slidably received in slot 36 defined by inflow housing 14. While inserted within slot 36, plate 16 prevents the medical device from passing from inflow housing 14 to outflow housing 12 while coupling an end of the medical device to the delivery system. In some embodiments, plate 16 comprises a body portion 62. Body portion 62 is configured to extend into the channel extending from third proximal open end 30 to fourth distal open end 32. In some embodiments, body portion 62 has a length substantially equal to an inner dimension of the channel at slot 36. Body portion 62 can define, in some embodiments, a slot 64. Slot 64 can be configured to allow a delivery device or first elongated member 18 to pass through, but configured to prevent a valve prosthesis from passing through the channel extending from third proximal open end 30 to fourth distal open end 32 of inflow housing 14.

In some embodiments, plate 16 further comprises at least one detent protrusion 68 for maintaining body portion 62 within the channel extending from third proximal open end 30 to fourth distal open end 32. For example, as shown in FIG. 1C, plate 16 includes two detent protrusions 68. Protrusions 68 engage inflow housing 14 to substantially prevent movement of plate 16 relative to inflow housing 14 until a user intentionally removes plate 16.

Plate 16 can further comprise, in some embodiments, a handle portion 66. Plate 16 is configured such that handle portion 66 remains outside inflow housing 14 when body portion 62 extends into the channel extending from third proximal open end 30 to fourth distal open end 32. Handle portion 66 provides an ergonomical area that is easily accessible to a user to grab and subsequently remove plate 16 from slot 36 defined by inflow housing 14.

Figure 2:
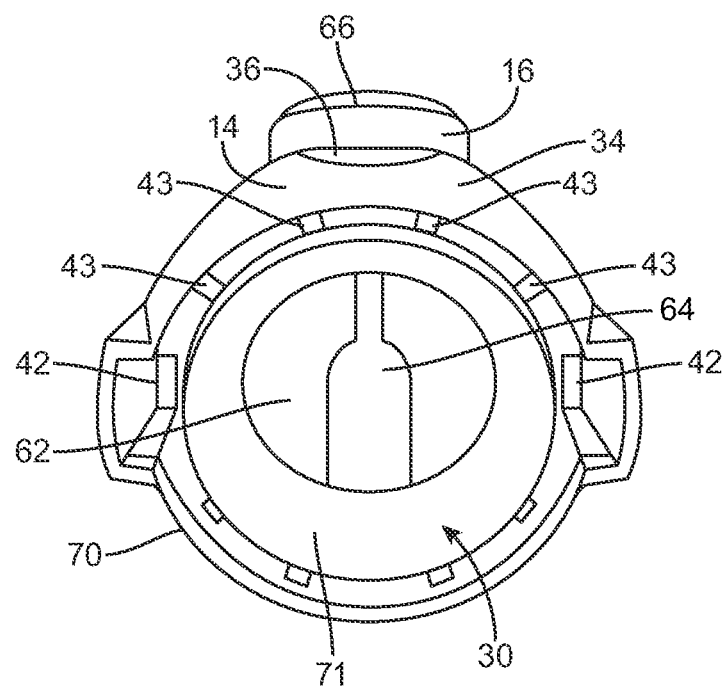
FIG. 2 illustrates a proximal view of the inflow housing of FIG. 1 according to an embodiment.

FIG. 2 is a proximal view of inflow housing 14 with plate 16 slidably and fully received in slot 36. In some embodiments, when plate 16 is in slot 36, body portion 62 of at least partially obstructs the channel extending from third proximal open end 30 to fourth distal open end 32 to prevent a valve prosthesis from distally advancing within the channel defined by inflow housing 14.

Inflow housing 14 can define at least one cavity 42 for receiving engagement tabs 28 of outflow housing 12. For example, as shown in FIG. 2, inflow housing 14 defines two opposing cavities 42 for receiving two engagement tabs 28 of outflow housing 12. In some embodiments, cavities 42 can be configured to create a snap or interference fit with engagement tabs 28. The position and shape of cavities 42 correspond to the position and shape of engagement tabs 28.

In some embodiments, first portion 34 of inflow housing 14 can be configured to create an interference fit with an end of a valve prosthesis. First portion 34 of inflow housing 14 can comprise an outer surface 70 and a spaced apart inner surface 71. An inner dimension of inner surface 71 is slightly smaller than an outer dimension of a valve prosthesis in an expanded state, creating an interference when the valve prosthesis is inserted in the channel defined by inner surface 71. The inner dimension of inner surface 71 can be varied based upon the size of the valve prosthesis being implanted. In some embodiments, inner surface 71 is tapered with an inner dimension decreasing in a direction from proximal open end 30 to distal open end 32. The tapered surface can help guide the prosthesis into the channel defined by inner surface 71.

Inflow housing 14 can further comprise, in some embodiments, a plurality of openings 43 defined by, for example, exterior surface 70 of inflow housing 14. Openings 43 allow air bubbles within the channel extending from third proximal open end 30 to fourth distal open end 32 to escape. Openings 43 help keep the medical device submerged in a solution, for example, a saline solution, during loading and prevent air from entering the capsule of the delivery device. The plurality of openings 43 can be located between outer surface 70 and inner surface 71.

Referring back to FIG. 1D, first elongated member 18 is configured to allow a tip of a delivery device to pass atraumatically through the medical device and to spread open one end of the medical device, for example, the outflow crowns and paddles of a valve prosthesis, to align the coupling members of the medical device with the coupling members of the attachment member of the delivery device as described below. First elongated member 18 can comprise a main body portion 44. Main body portion 44 defines a channel having an open end 46. In some embodiments, main body portion 44 has a substantially cylindrical outer surface. The outer diameter of main body portion 44 is smaller than an inner dimension of distal open end 22 and second proximal open end 24 of outflow housing 12, and smaller than an inner dimension of proximal open end 30 and distal open end 32 of inflow housing 14, so main body portion 44 can pass through the channel collectively defined by outflow housing 12 and inflow housing 14 (and slot 64 defined by body 62 of plate 16).

Figure 1D:
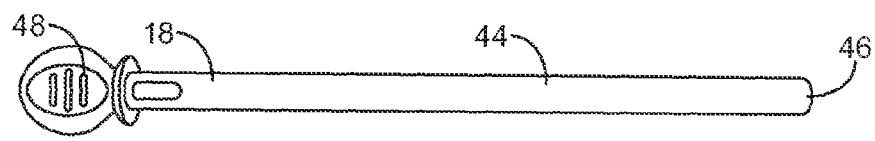

First elongated member 18 can comprise, in some embodiments, a handle portion 48. Handle portion 48 can be ergonomically designed to facilitate easy handling by a user. For example, as shown in FIG. 1D, handle portion 48 can have a substantially flat paddle shape. Main body portion 44 has an axial length such that, when outflow housing 12 is coupled to inflow housing 14 and main body portion 44 passes through the channel collectively defined by outflow housing 12 and inflow housing 14, open end 46 extends beyond proximal open end 24 of outflow housing 12 and handle portion 48 extends beyond distal open end 32 of inflow housing 14. In some embodiments, handle portion 48 has an outer dimension that is larger than the inner dimension of distal open end 32. In such embodiments, handle portion 48 can function as a stop preventing further proximal movement of first elongated member 18 relative to inflow housing 14. In some embodiments, when handle portion 48 abuts distal open end 32 of inflow housing 14, open end 46 of first elongated member 18 extends beyond second proximal open end 24 of outflow housing 12. In some embodiments, main body portion 44 has an axial length such that when handle portion 48 abuts distal open end 32 of inflow housing 14, open end 46 extends beyond the coupling members of a medical device extending from open end 24 of outflow housing 12.

The inner diameter of open end 46 is sized to receive a tip of the delivery system. The outer diameter of main body portion 44 is sized so that main body portion 44 can pass through the channel collectively defined by outflow housing 12 and inflow housing 14 (and slot 64 defined by body 62 of plate 16).

Figure 1E:
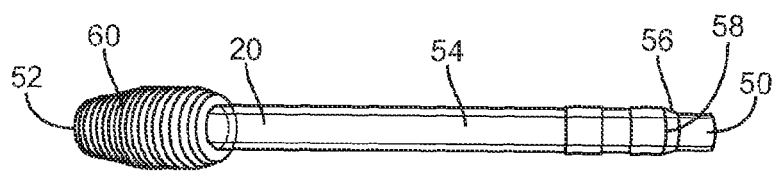

Main body portion 44 isolates and protects the medical device, for example, the valve material of a prosthetic valve, from a delivery system passing through the medical device. Turning to FIG. 1E, second elongated member 20 is configured to provide additional column support for protecting a distal portion of the delivery device, for example, a capsule of a delivery catheter, during loading; to notify a user of a potential misload; and to interface the coupling members of the medical device, for example, paddles of a valve prosthesis, with the coupling members of the attachment member of the delivery device, for example, recesses in a spindle of a delivery catheter. Second elongated member 20 is also configured to allow for inspection by a user that correct coupling has occurred, for example, that the paddles are correctly seated within the recess. Second elongated member 20 comprises a main body portion 54. Main body portion 54 defines a channel having a distal open end 50 and a proximal open end 52. In some embodiments, main body portion 54 has a substantially cylindrical outer surface. Main body portion 54 can protect a capsule of the delivery device by reducing or preventing the capsule from excessively bowing or being pinched by the user via additional column support.

Second elongated member 20 can also comprise a tip 56. In some embodiments, tip 56 is elastomeric. In some embodiments, tip 56 has a tapered outer surface; the outer dimension of tip 56 decrease in a direction from open end 52 to open end 50. The outer dimension of main body portion 54 and tip 56 is smaller than an inner dimension of distal open end 22 and second proximal open end 24 of outflow housing 12, and smaller than an inner dimension of proximal open end 30 and second portion 38, so main body portion 54 and tip 56 can pass into the channel collectively defined by outflow housing 12 and inflow housing 14. In some embodiments, an inner dimension of tip 56 is smaller than an outer dimension of a tip of a delivery device. In some embodiments, an interior surface of main body portion 54 defines a shoulder surface 58 that extends radially inward. Shoulder surface 58 can be sized to prevent a capsule of a delivery device from distally advancing past shoulder surface 58 and through open end 50 and into tip portion 56.

In some embodiments, a portion of main body portion 54 adjacent and proximal to shoulder surface 58 is configured to prevent the capsule of a delivery system from expanding during loading. In some embodiments, this portion of main body portion 54 adjacent shoulder surface 58 is a tight tolerance area that provides a tight fit with the capsule of the delivery system and substantially prevents the capsule from expanding during loading. In some embodiments, the inner dimension of a portion of main body portion 54 adjacent shoulder surface 58 is sized such that if there is a misload between the delivery catheter and the medical device, a noticeable increase in the amount of force required to load the medical device within the capsule will occur because the outer dimension of the medical device will be larger than the inner dimension of the portion of main body portion 54 adjacent shoulder surface 58.

Second elongated member 20 can comprise, in some embodiments, a handle portion 60. Handle portion 60 can be ergonomically designed to facilitate easy handling of first elongated member 18. In some embodiments, handle portion 60 extends radially outward from main body portion 54. For example, as shown in FIG. 1E, handle portion 60 can have a bulb shape. Main body portion 54 can have an axial length such that when handle portion 60 abuts proximal open end 24 of outflow housing 12, open end 50 is adjacent a proximal end of third portion 40 of inflow housing 14.

In some embodiments, handle portion 60 has an outside diameter that is larger than the inside diameter of proximal open end 24 of outflow housing 12. In such embodiments, handle portion 60 can function as a stop preventing further distal movement of second elongated member 20 relative to outflow housing 12.

In some embodiments, at least one portion of one or more components of the system is transparent. For example, outflow housing 12, inflow housing 14, plate 16, elongated member 18, and second elongated member 20 can each be transparent. This transparency allows a user to visually verify the proper orientation and coupling of a valve prosthesis being loaded as further described below.

Components of the loading system can made of any suitable material or materials. For example, the inflow housing 14, outflow housing 12, plate 16, first elongated member 18, and second elongated member 20 may be made of materials commonly used in medical device applications. For example, suitable polymeric materials or metals, such as stainless steel, may be used.

Figure 7:
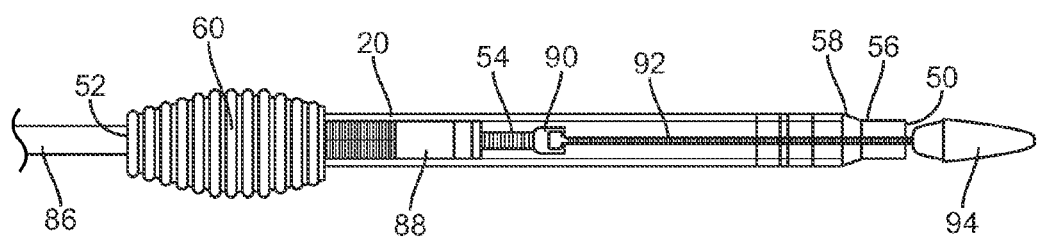

In use, the loading system facilitates loading a valve prosthesis onto a delivery device, for example, a transfemoral, transapical, or direct-aortic approach minimally invasive delivery catheter 86 (a distal portion of which is shown in FIG. 7). (In some transapical approach embodiments, the inflow end of the medical device comprises the paddles, instead of the outflow end as illustrated in the Figures.)

FIGS. 3-14 illustrate a method of loading a medical device onto a delivery device according to an embodiment. As discussed below, in some embodiments, some or all of the steps of loading a valve prosthesis are performed in a liquid bath, for example, a cold saline bath. Accordingly, in some embodiments, the material(s) used for components of system are relatively dimensionally stable when exposed to temperatures at or relatively near the temperature of the liquid bath being used.

Figure 3:
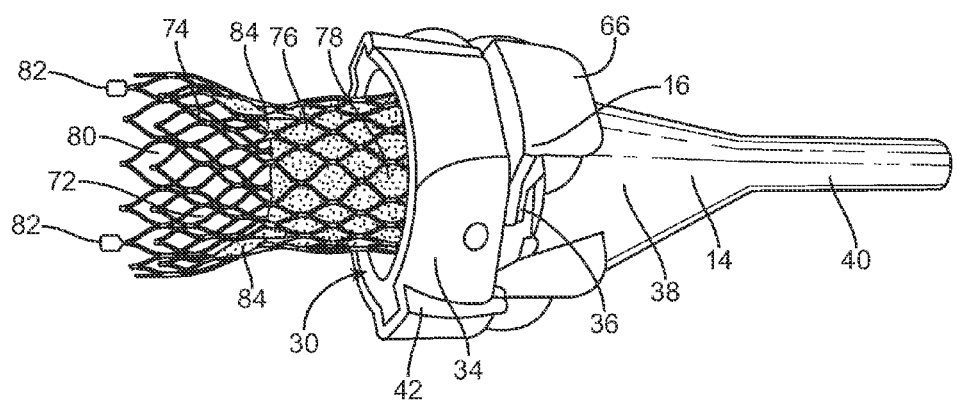
Figure 8:
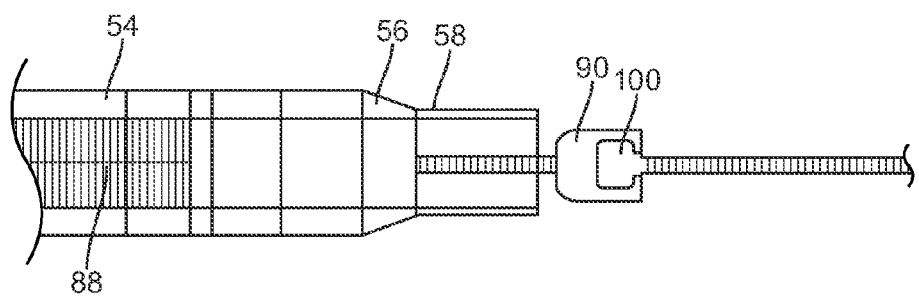

Referring to FIG. 3, the loading system is used to load a medical device, for example, a valve prosthesis 72, onto a delivery device, for example, a delivery catheter 86 as shown in FIGS. 7 and 8. Valve prosthesis 72 can be an aortic valve prosthesis, a mitral valve prosthesis, or any other suitable valve prosthesis. Valve prosthesis 72 can comprise a frame 74 and a valve assembly 76 coupled to frame 74. Valve prosthesis 72 can be self-expandable or balloon expandable. Valve prosthesis 72 comprises an inflow end 78 and an outflow end 80. In some embodiments, at outflow end 80, frame 74 comprises at least one coupling member, for example, an eyelet, a paddle, or any other suitable coupling member configuration, that extends beyond the outflow crowns of frame 74. Valve assembly 76 can comprise a plurality of commissures 84. Valve prosthesis 72 can comprise at least one coupling member 82, for example, a paddle (as shown in FIG. 3), eyelet, loop, slot, or any other suitable coupling member. In some embodiments, valve prosthesis 72 comprises a pair of paddles 82 on opposing sides of prosthesis 72. But in some embodiments, a greater or lesser number of coupling members 82 may be provided.

Although the figures illustrate the loading system with a valve prosthesis, the loading system can be used to deliver any suitable medical device, for example, implants, stents, and other implantable or temporary prostheses that do not include a valve assembly.

As illustrated in FIG. 3, valve prosthesis 72 can be initially and releasably coupled with inflow housing 14 while plate 16 is slidably received within slot 36 of inflow housing 14. Inflow end 78 of valve prosthesis 72 can be aligned and inserted in the cavity defined by inner surface 71 of first portion 34 of inflow housing 14. As discussed above, an inner surface of first portion 34 can be sized to create an interference fit with inflow end 78 of valve prosthesis 72. In some embodiments, valve prosthesis 72 can be oriented such that coupling members 82 are substantially in a vertical plane. At this seated position, inflow end 78 of valve prosthesis 72 is adjacent to and, in some embodiments, abuts plate 16.

Figure 4:
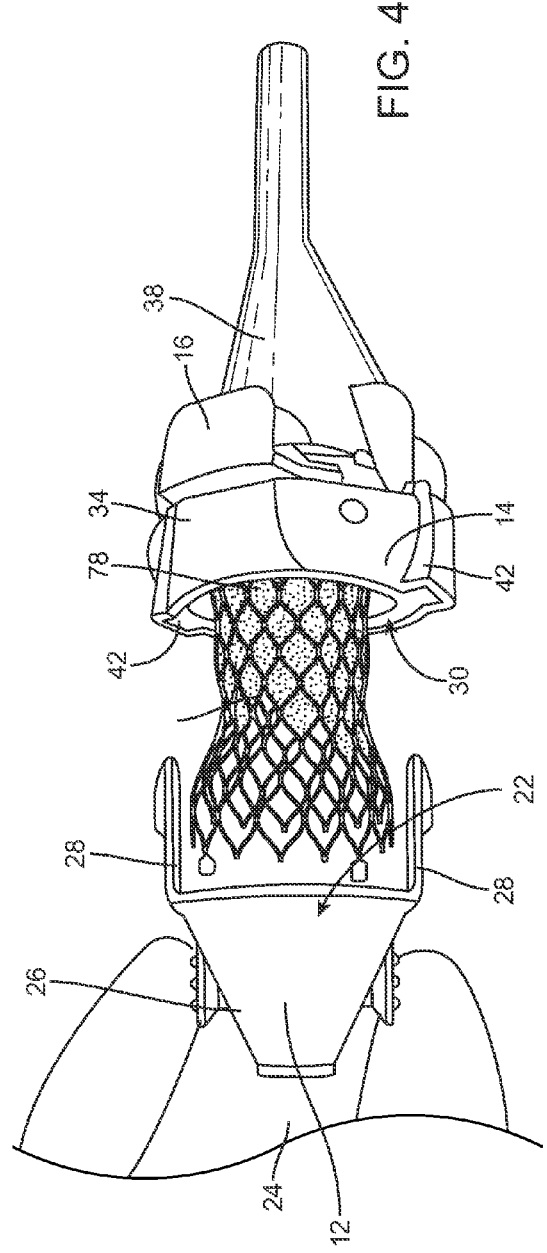
Figure 5:
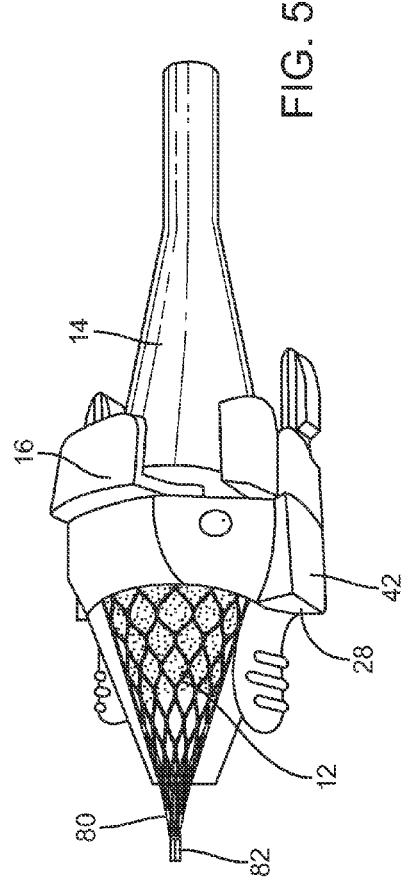

Then, as illustrated in FIGS. 4 and 5, valve prosthesis 72 is advanced along the tapered interior surface of portion 26 of outflow housing 12 to compress outflow end 80 of valve prosthesis 72. In some embodiments, this compression step occurs by advancing outflow housing 12, with distal open end 22 facing valve prosthesis 72, towards valve prosthesis 72 seated in inflow housing 14. Outflow housing 12 can be advanced until distal open end 22 of outflow housing 12 is adjacent open end 30 of inflow housing 14 and outflow housing 12 and inflow housing 14 are coupled, as shown in FIG. 5. Plate 16 in slot 36 of inflow housing 14 can apply an axial force to advance prosthesis 72 relative to outflow housing 12 into a desired final position within outflow housing 12. For example, inflow end 78 of valve prosthesis 72 contacts body portion 62 of plate 16.

In some embodiments, when distal open end 22 of outflow housing 12 is adjacent open end 30 of inflow housing 14, engagement tabs 28 of outflow housing 12 engage cavities 42 defined by inflow housing 14, for example, by a snap or interference fit.

At this point, in some embodiments, at least a portion of outflow end 80 of valve prosthesis 72, including, for example, coupling members 82, extend from proximal open end 24 of outflow housing 12. The tapered inner surface of portion 26 of the outflow housing 12 reduces an external dimension of at least a portion of valve prosthesis 72 as prosthesis 72 is moved proximally and relative to outflow housing 12.

In some embodiments, this coupling step is performed in a liquid bath, and the coupled inflow housing 14 and outflow housing 12 can be gently agitated while submerged in the bath to release any air bubbles contained in valve prosthesis 72, which in turn can pass through openings 43 of inflow housing 14.

Figure 6:
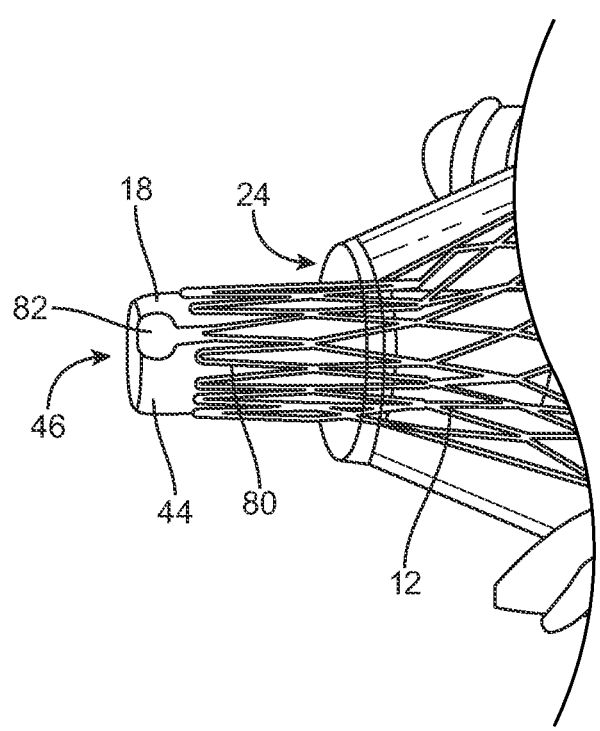

Referring to FIG. 6, after prosthesis 72 is positioned within outflow housing 12 and after outflow housing 12 is coupled to inflow housing 14, first elongated member 18 can be introduced into distal open end 32 of inflow housing 14 and advanced within inflow housing 14 and outflow housing 12 until first elongated member 18 contacts outflow end 80 of valve prosthesis 72 and, specifically in some embodiments, an inner surface of frame 74 of prosthesis 72. Movement of first elongated member 18 in a proximal direction through prosthesis 72 can properly orient leaflets of valve assembly 76 such that the risk of damaging the leaflets is reduced while valve prosthesis 72 is further reduced. In some embodiments, first elongated member 18 is further advanced to pass through proximal open end 24 of outflow housing 12 such that first elongated member 18 contacts the portion of valve prosthesis 72 extending beyond proximal open end 24 as shown in FIG. 6. This contact expands this portion of outflow end 80 of prosthesis 72, spreading open the outflow crowns of frame 74. In some embodiments, first elongated member 18 contacts the portion of valve prosthesis 72 extending beyond proximal open end 24 when handle portion 48 of first elongated member 18 is adjacent to or, in some embodiments, abuts distal open end 32 of inflow housing 14. At this point, a user can inspect the outflow crowns of frame 74 to ensure that the crowns are evenly spaced and that coupling members 82 are opposite from each other. If a misalignment exists, a user can manually adjust the outflow crowns to achieve the desired configuration. For example, a user can directly inspect the outflow crowns directly facing the user, and can indirectly inspect the outflow crowns facing away from the user by using mirror 98 of tray 96.

In some embodiments, the loading system is used to load a medical device on a delivery catheter 86 as shown in FIGS. 7-14. Delivery catheter 86 comprises a capsule 88 and delivery shaft 92 movably received within capsule 88. A proximal end (not shown in FIGS. 7-14) of delivery catheter 86 actuates movement of delivery shaft 92 relative to capsule 88. The proximal end may comprise a handle of any suitable style or shape to permit grasping by a user of the catheter 86. Delivery catheter 86 can further comprise an attachment member 90 attached to delivery shaft 92 that is configured to couple a valve prosthesis to delivery catheter 86. In some embodiments, attachment member 90 is a spindle. In some embodiments, as best seen in FIG. 8, attachment member 90 comprises at least one coupling member 100, for example, two opposing coupling members 100. As shown in FIG. 8, coupling members 100 can be recesses sized and shaped to closely correspond to the size and shape of coupling members of a valve prosthesis. Delivery catheter 86 can also comprise a distal tip 94 coupled to delivery shaft 92. In some embodiments, tip 94 is sized to substantially close off an open distal end of capsule 88 when delivery shaft 92 is retracted sufficiently relative to capsule 88. Tip 94 can also have an atraumatic shape to minimize damage to the vasculature through which catheter 86 may travel. Delivery catheter 86 can have any conventional or suitable shape and made from any suitable material.

To load a valve prosthesis on delivery catheter 86, a tray 96 forming a cavity for holding a liquid can be used as shown in FIG. 7. Tray 96 can comprise a mirror 98 in the cavity. Mirror 98 allows a user to visually and quickly verify the proper orientation and coupling of a valve prosthesis on a side of delivery catheter 86 facing away from the user. In some embodiment, tray 96 can be configured as described in U.S. application Ser. No. 13/658,082, filed Oct. 23, 2012, which is incorporated by reference herein.

In some embodiments, delivery shaft 92 is advanced distally relative to capsule 88 to place delivery catheter 86 in an open configuration—tip 94 does not close capsule 88 and attachment member 90 is outside of capsule 88. Then, second elongated member 20 is advanced over delivery catheter 86. For example, tip 94, attachment member 90, and capsule 88 are distally advanced relative to second elongated member 20 through the channel defined by elongated member 20 from open end 52 to open end 50. In some embodiments, delivery catheter 86 is advanced distally relative to second elongated member 20 until attachment member 90 passes through open end 50 and is distal to tip 56.

Figure 9:
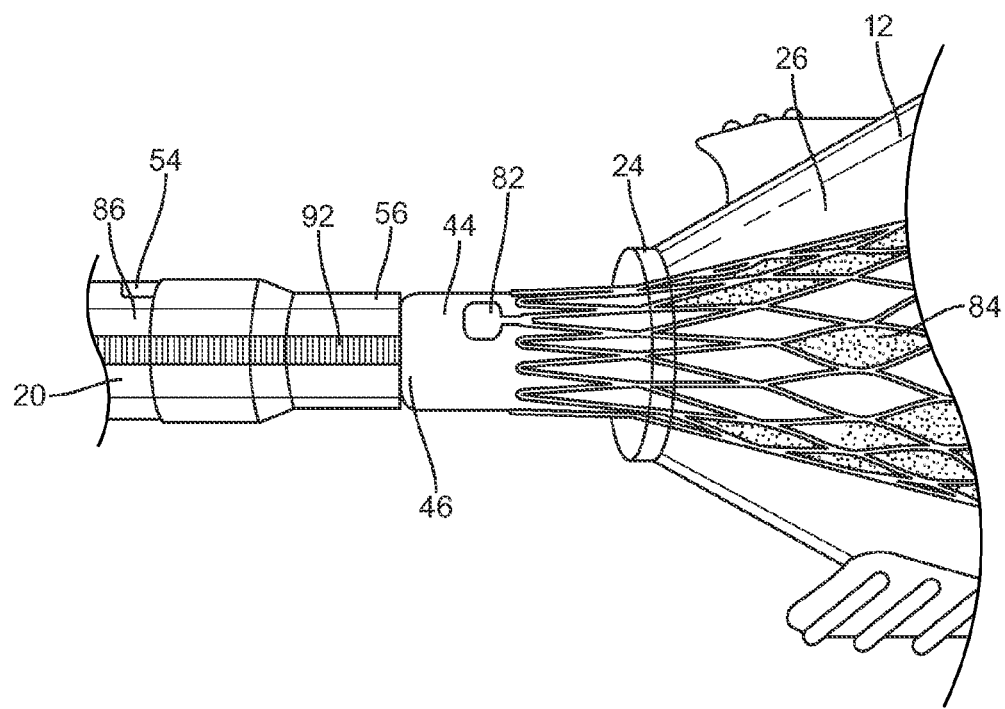

Next, referring to FIG. 9, second elongated member 20 encompassing delivery catheter 86 is advanced towards open end 46 of first elongated member 18 such that attachment member 90 of delivery catheter 86 passes through open end 46 of first elongated member 18 and into the channel defined by body portion 44 of first elongated member 18. Coupling members 100 of attachment member 90 are radially aligned with respective coupling members 82 of valve prosthesis 72.

Figure 10C:
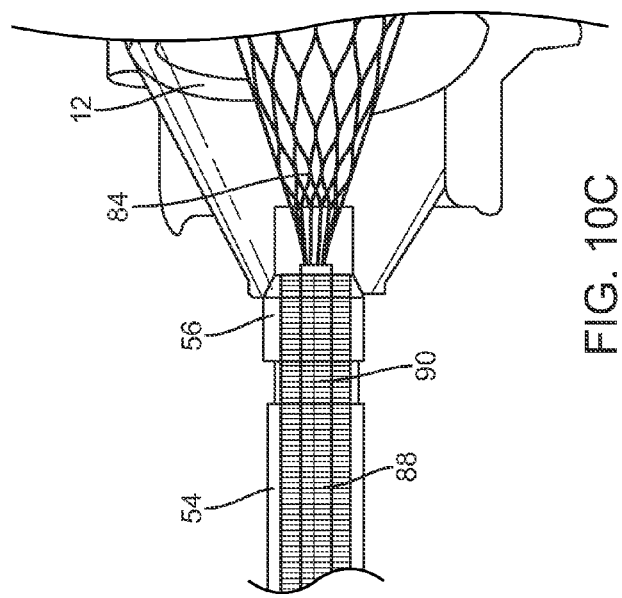
FIGS. 10A-10C are enlarged perspective views of an outflow housing, a valve prosthesis, a second elongated member, and a delivery device at loading steps according to an embodiment.
Figure 10A:
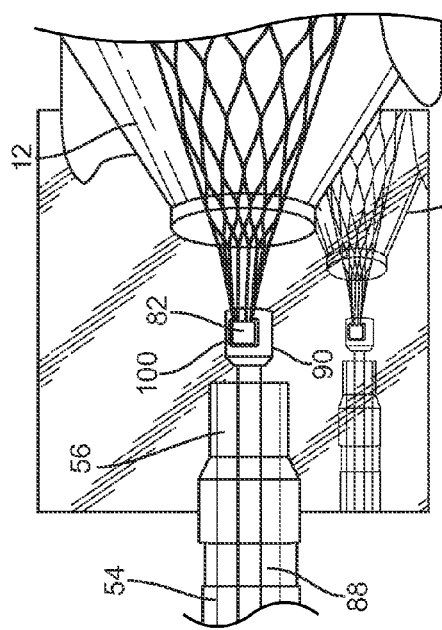

And then, as shown in FIG. 10A, first elongated member 18 is distally advanced relative to valve prosthesis 72 and delivery catheter 86, releasing contact between first elongated member 18 and outflow portion 80 of valve prosthesis 72 extending beyond proximal open end 24. The contact release allows outflow portion to contract such that coupling members 100 of attachment member 90 of delivery catheter 86 engage coupling members 82 of valve prosthesis 72. For example, in some embodiments in which coupling members 100 are recesses defined by attachment member 90 and coupling members 82 of prosthesis 72 are paddles, paddles 82 are inserted into recesses 100. At this point, a user can inspect that coupling members 82 of prosthesis 72 are correctly coupled to coupling members 100 of attachment member 90. For example, a user can inspect that paddles 82 of prosthesis 72 are correctly seated within recesses 100 of attachment member 90. A user can directly inspect this coupling facing the user, and can indirectly inspect the coupling facing away from the user by using mirror 98 of tray 96. If a misalignment exists, a user can manually adjust the coupling members 82 and 100 to achieve the desired seating configuration.

Figure 10B:
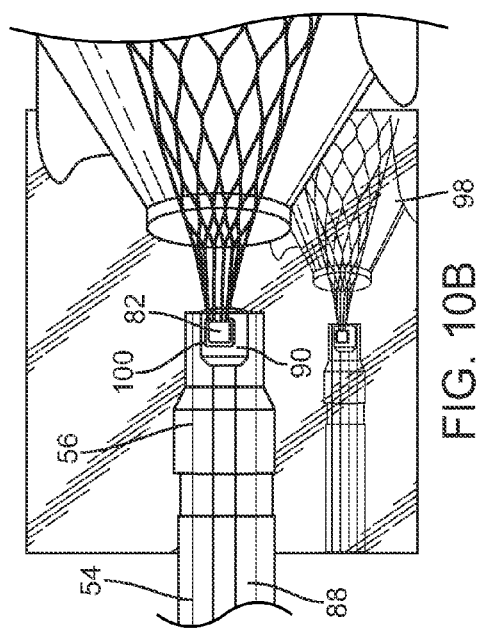

As shown in FIGS. 10A-10C, after coupling valve prosthesis 72 to delivery catheter 86 via attachment member 90, attachment member 90 and valve prosthesis 72 are advanced proximally relative to second elongated member 20 to secure coupling members 82 of valve prosthesis and attachment member 90 at least partially (and in some embodiments fully) within the channel defined by tip 56. In some embodiments in which elastomeric tip 56 is transparent, a user can visually inspect that coupling members 82 of prosthesis 72 are still correctly coupled to coupling members 100 of attachment member 90 while within the channel defined by tip 56. Again, a user can directly inspect the coupling facing the user, and can indirectly inspect the coupling facing away from the user by using mirror 98 of tray 96.

As shown in FIG. 10B, attachment member 90 and valve prosthesis 72 are further advanced proximally relative to second elongated member 20 until the outflow crowns of frame 74 are compressed adjacent to attachment member 90. At this point, a user can again visually verify that coupling members 82 of prosthesis 72 are correctly coupled to coupling members 100 of attachment member 90 while within the channel defined by second elongated member 20.

Attachment member 90 and valve prosthesis 72 can be further advanced proximally relative to second elongated member 20 until coupling members 82 of valve prosthesis 72 or the outflow crowns of frame 74 are at least partially within capsule 88 of delivery catheter 86. Again, a user can visually verify that coupling members 82 of prosthesis 72 are still correctly coupled to coupling members 100 of attachment member 90 while within the channel defined by second elongated member 20.

In some embodiments, as illustrated in FIG. 10C, attachment member 90 and valve prosthesis 72 are further advanced proximally relative to second elongated member 20 until commissures 84 are adjacent tip 56 of second elongated member 20. In some embodiments, catheter 86 comprises a tactile feedback mechanism, for example, protrusions on a proximal handle portion (not shown), to indicate when to stop proximally advancing attachment member 90 and valve prosthesis 72 relative to capsule 88. In some embodiments in which second elongated member 20, including for example, elastomeric tip 56, are transparent, a user can visually verify that coupling members 82 of prosthesis 72 are still correctly coupled to coupling members 100 of attachment member 90 while within the channel defined by second elongated member 20. Again, a user can directly inspect the coupling facing the user, and indirectly inspect the coupling facing away from the user by using mirror 98 of tray 96.

Figure 12A:
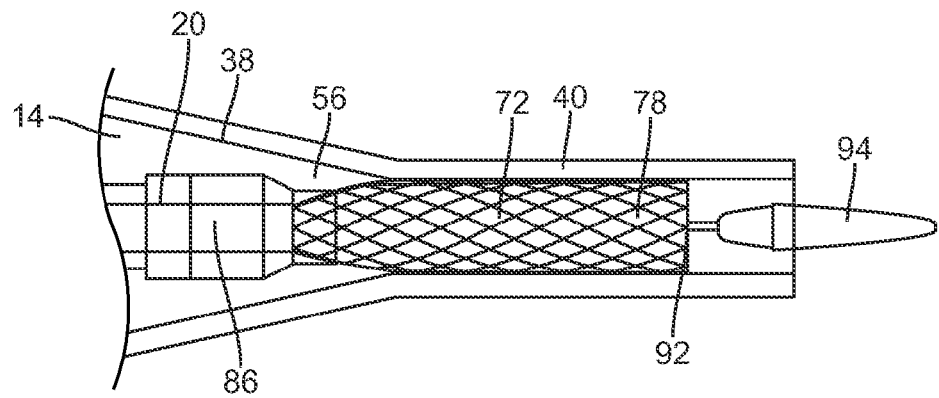
FIGS. 12A-12B are enlarged side views of an inflow housing, a valve prosthesis, and a delivery device at loading steps according to an embodiment.

Now referring to FIGS. 11A, 11B, and 12A, plate 16 (as shown in FIG. 3) is removed from or repositioned within slot 36 defined by inflow housing 14 such that body portion 62 of plate 16 no longer obstructs the channel collectively defined by outflow housing 12 and inflow housing 14. With plate 16 removed (or repositioned), second elongated member 20 and valve prosthesis 72 can be advanced distally (in the direction of arrow A) relative to coupled outflow housing 12 and inflow housing 14 to crimp all or at least a portion of valve prosthesis 72 not within capsule 88. As second elongated member 20 and valve prosthesis 72 are advanced proximal, inflow end 78 of prosthesis 72 contacts the tapered inner surface of portion 38 of inflow housing 14, compressing inflow end 78 of prosthesis 72. In some embodiments, second elongated member 20 can be advanced proximally until all or at least a portion of valve prosthesis 72 not within capsule 88 is positioned within the channel defined by third portion 40 as shown in FIGS. 11B and 12A. In some embodiments, second elongated member 20 and valve prosthesis 72 are advanced distally relative to inflow housing 14 until tip 56 is adjacent to or, in some embodiments, abuts the proximal end of third portion 40. In some embodiments, this position occurs when handle portion 60 of second elongated member 20 is adjacent to or, in some embodiments, abuts second proximal open end 24 of outflow housing 12.

Figure 12B:
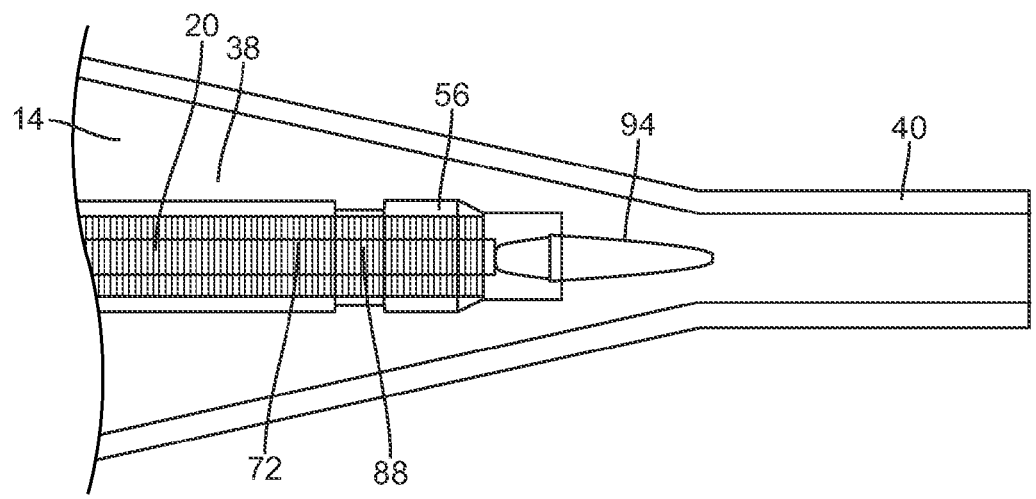

In some embodiments, when valve prosthesis 72 is within cylindrical portion 40 of inflow housing 14, valve prosthesis 72 has a compressed diameter substantially equal to or less than an inner dimension of capsule 88. This way, prosthesis 72 can easily fit within capsule 88 of the catheter 86. As illustrated in FIG. 12B, the delivery shaft 92 and valve prosthesis 72 can be advanced proximally relative to capsule 88 to retract valve prosthesis 72 within capsule 88. In some embodiments, while valve prosthesis 72 is retracted within capsule 88, second elongated member 20 closely encompasses capsule 88 to reduce radial expansion of capsule 88 from any radial force transmitted to capsule 88.

Figure 13:
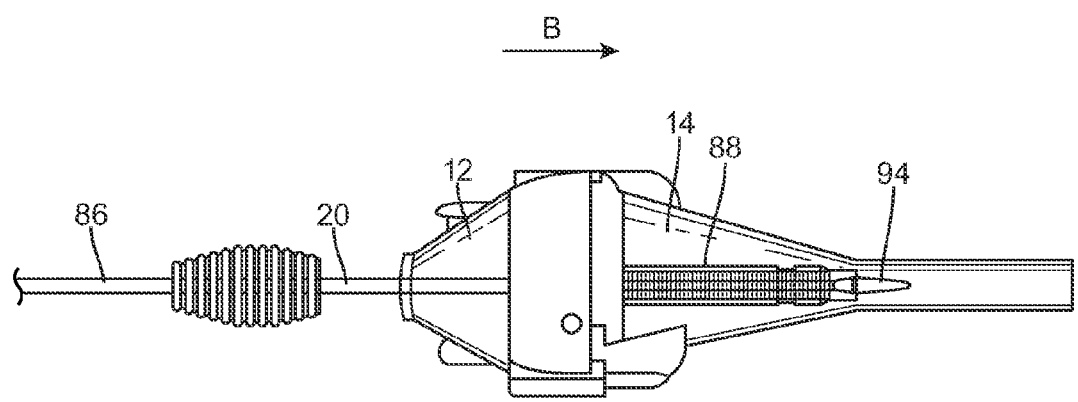
Figure 14:
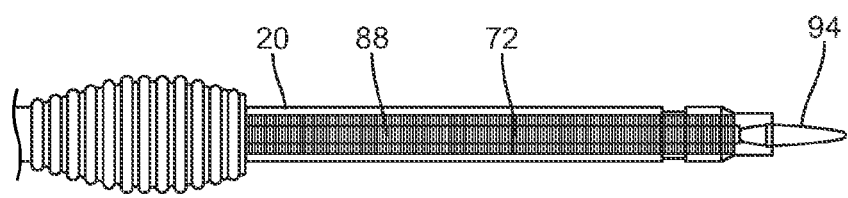

As illustrated in FIG. 13, once valve prosthesis 72 is either fully or at least partially retracted within capsule 88, outflow housing 12 and inflow housing 14 can be removed by distally advancing (in direction of arrow B) outflow housing 12 and inflow housing 14 relative to and over delivery catheter 86. In some embodiments, outflow housing 12 and inflow housing 14 can be removed without decoupling each component from each other.

In some embodiments, attachment member 90 and valve prosthesis 72 are further advanced proximally relative to capsule 88 until tip 94 is adjacent to or, in some embodiments, abuts capsule 88.

And then, second elongated member 20 can removed from delivery catheter 86 by distally advancing second elongated member 20 over delivery catheter 86.

At this point, valve prosthesis 72 can be delivered to a desired implantation site within a patient's vasculature or heart.

One or more of the above described loading steps can be performed within a liquid bath, for example, a cold saline bath.

Figure 15:
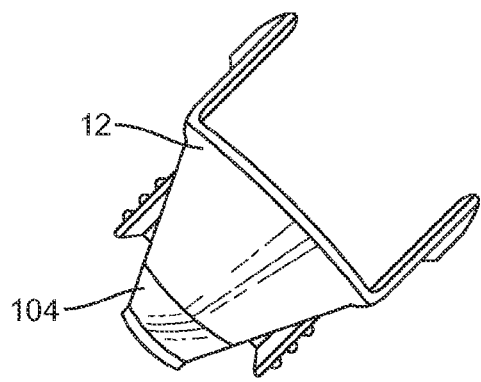
FIG. 15 is a perspective view of an outflow housing of a loading system according to another embodiment.
Figure 16:
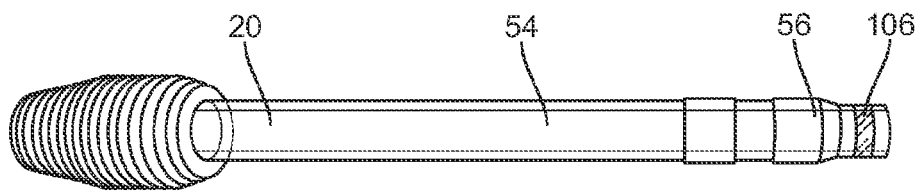
FIG. 16 is a perspective view of a second elongated component of a loading system according to another embodiment.

In some embodiment, one or more components of the loading system can comprise one or more portions configured to provide a magnified image of a portion of a valve prosthesis located in a channel defined by the component. For example, the component can form a lens type surface, for example, a convex surface, that magnifies the image of the valve prosthesis. The magnified image can make visual verification of valve prosthesis orientation and coupling easier and quicker for a user. For example, FIG. 15 is a perspective view of an outflow housing 12 of a loading system according to an embodiment. Outflow housing 12 comprises a portion 104 configured to provide a magnified image of a portion of a valve prosthesis positioned within a channel defined by outflow housing 12. As shown in FIG. 15, portion 104 circumferentially surrounds outflow housing 12. In some embodiments, however, portion 104 can be a discrete and non-circumferential portion. FIG. 16 is a perspective view of a second elongated component 20 of a loading system according to an embodiment. Second elongated member 20 comprises a portion 106 at tip 56 that is configured to provide a magnified image of a portion of a valve prosthesis positioned within a channel defined by second elongated member 20. As shown in FIG. 15, portion 106 circumferentially surrounds outflow housing 12. In some embodiments, however, portion 106 can be a discrete and non-circumferential. In some embodiments, portion 106 can be located along main body portion 54.

In some embodiments, mirror 98 creates a magnified image of the valve prosthesis 72 and delivery system 86.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A system for loading a medical device onto a delivery system, comprising:
   a first housing comprising a first open end, a first tapered inner surface, and a second open end, the first open end having an inner dimension that is smaller than an inner dimension of the second open end;
   a second housing comprising a third open end, a second tapered inner surface, and a fourth open end, the second housing defining a slot between the second tapered inner surface and the third open end, the fourth open end having an inner dimension that is smaller than an inner dimension of the third open end; and
   a plate separate from the first housing and the second housing, the plate configured to be slidably received within the slot.

2. The system of claim 1, wherein the second housing is configured to be selectively coupled to the first housing.

3. The system of claim 1, wherein the second housing further comprises a first portion defining a channel adjacent to the third open end configured to receive a medical device and create an interference fit between the medical device and the second housing.

4. The system of claim 1, wherein the second housing further comprises a first cylindrical interior surface adjacent to the second tapered inner surface at one end and adjacent to the fourth open end at an opposite end.

5. The system of claim 1, wherein the plate defines a plate slot configured to allow a shaft to pass through the plate and the second housing with the plate received in the slot of the second housing.

6. The system of claim 1, further comprising a first elongated member comprising a body and an elastomeric tip collectively defining a channel, the channel being configured to receive a distal tip and an attachment portion of a delivery system onto which the medical device will be loaded.

7. The system of claim 6, wherein the elastomeric tip and the body are transparent.

8. The system of claim 6, wherein the elastomeric tip comprises a portion configured to provide a magnified image of a portion of a valve prosthesis located in the channel defined by the first elongated member.

9. The system of claim 1, further comprising a second elongated member comprising a body configured to pass through the third and fourth open ends of the second housing and the first and second open ends of the first housing, the body of the second elongated member defining a channel configured to receive a distal tip and an attachment portion of a delivery system onto which the medical device will be loaded.

10. The system of claim 1, wherein the first housing comprises a portion configured to provide a magnified image of a portion of a valve prosthesis located in channel defined by the first housing.

11. A system for loading a medical device onto a delivery system, comprising:
- a first housing comprising a first open end, a second open end, and a first channel extending from the first open end to the second open end, the first open end having an inner dimension that is smaller than an inner dimension of the second open end;
- a second housing comprising a third open end, a fourth open end, and a second channel extending from the third open end to the fourth open end, the second housing defining a slot extending through a surface of the housing and into the second channel, the fourth open end having an inner dimension that is smaller than an inner dimension of the third open end; and
- a plate configured to be slidably received within the slot such that a portion of the plate extends transversely into the second channel and at least partially blocks the second channel.

12. The system of claim 11, wherein the second housing is configured to be selectively coupled to the first housing.

13. The system of claim 11, wherein the second channel includes a tapered portion and a cylindrical portion, wherein the cylindrical portion is disposed between the tapered portion and the fourth open end.

14. The system of claim 11, further comprising a first elongated member comprising a body and a tip collectively defining a third channel, the third channel being configured to receive a distal tip and an attachment portion of a delivery system onto which the medical device will be loaded.

15. The system of claim 14, further comprising a second elongated member comprising a body configured to pass through the third and fourth open ends of the second housing and the first and second open ends of the first housing, the body of the second elongated member defining a fourth channel configured to receive the distal tip and the attachment portion of the delivery system onto which the medical device will be loaded.

16. The system of claim 15, wherein the plate defines a plate slot, wherein the plate slot is sized such that the second elongated member may pass through the plate slot with the plate disposed in the slot of the second housing.

17. The system of claim 11, wherein the first housing comprises a portion configured to provide a magnified image of a portion of a valve prosthesis located in channel defined by the first housing.

18. A system for loading a medical device onto a delivery system, comprising:
- a first housing comprising a first open end, a second open end, and a first channel extending from the first open end to the second open end, the first open end having an inner dimension that is smaller than an inner dimension of the second open end;
- a second housing comprising a third open end, a fourth open end, and a second channel extending from the third open end to the fourth open end, the fourth open end having an inner dimension that is smaller than an inner dimension of the third open end, wherein the second channel includes a first portion adjacent the third open end configured to receive an inflow portion of a medical device therein, wherein the second housing includes a blocking device for selectively blocking and unblocking a portion of the second channel, wherein with the blocking device in a blocking configuration, the medical device is prevented from moving from the first portion of the second channel towards the fourth open end;
- wherein the first housing is configured such that the second open end extends over an outflow portion of the medical device with the inflow portion of the medical device disposed in the first portion of the second housing;
- wherein the first housing is configured to be moved towards the second housing such that the second open end of the first housing is coupled to the third open end of the second housing to radially compress the outflow end of the medical device as the outflow end of the medical device passes from the second open end through the first open end of the first housing; and
- a first elongated member comprising a body and a tip collectively defining a third channel, the third channel being configured to receive a distal tip and an attachment portion of a delivery device, wherein the first elongate member is configured to be disposed adjacent to the second open end of the first housing such that the attachment portion of the delivery device may be coupled to the medical device;
- wherein with the blocking device in an unblocked configuration and the medical device attached to the attachment portion within the third channel of the first elongated member, the first elongated member is configured to push the medical device through the second channel of the second housing to radially compress the medical device.

19. The system of claim 18, wherein the blocking device comprises a plate configured to be received within a slot of the second housing, wherein with the plate disposed in the slot, the blocking device is in the blocking configuration such that the plate blocks at least a portion of the second channel, and with the plate removed from the slot, the blocking device is in the unblocked configuration such that the medical device may pass through the second channel.

20. The system of claim 18, wherein the second channel includes the first portion, a tapered portion extending from the first portion towards the fourth open end, and a cylindrical portion extending between the tapered portion and the fourth open end, wherein the cylindrical portion is sized to house the medical device in a radially compressed configuration.

* * * * *